United States Patent
Scampoli et al.

(10) Patent No.: US 11,553,918 B2
(45) Date of Patent: Jan. 17, 2023

(54) RELOAD ASSEMBLY WITH KNIFE CARRIER LOCKOUT

(71) Applicant: Covidien LP, Mansfield, MA (US)

(72) Inventors: David Scampoli, South Glastonbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 73 days.

(21) Appl. No.: 17/088,160

(22) Filed: Nov. 3, 2020

(65) Prior Publication Data

US 2021/0177422 A1   Jun. 17, 2021

Related U.S. Application Data

(60) Provisional application No. 62/948,400, filed on Dec. 16, 2019.

(51) Int. Cl.
*A61B 17/115* (2006.01)
*A61B 17/072* (2006.01)

(52) U.S. Cl.
CPC .... *A61B 17/1155* (2013.01); *A61B 17/07207* (2013.01); *A61B 2017/07271* (2013.01)

(58) Field of Classification Search
CPC .......... A61B 17/1155; A61B 17/07207; A61B 17/105; A61B 17/1114
See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |

(Continued)

FOREIGN PATENT DOCUMENTS

| CA | 908529 A | 8/1972 |
| CA | 2805365 A1 | 8/2013 |

(Continued)

OTHER PUBLICATIONS

European Search Report dated May 21, 2021, issued in corresponding EP Appln. No. 20214062, 6 pages.

*Primary Examiner* — Nathaniel C Chukwurah

(74) *Attorney, Agent, or Firm* — Carter, DeLuca & Farrell LLP

(57) ABSTRACT

A surgical stapling device includes a reload assembly that includes a dual-detent system to retain a knife carrier of the reload assembly in a retracted position after the stapling device is fired. The dual detent system includes auxiliary and primary detents to improve the retention force of the knife carrier to minimize the likelihood of inadvertent readvancement of the knife carrier and annular knife.

19 Claims, 14 Drawing Sheets

(56) References Cited

U.S. PATENT DOCUMENTS

| | | |
|---|---|---|
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant .................. A61B 17/115 227/19 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |

(56) References Cited

U.S. PATENT DOCUMENTS

| | | |
|---|---|---|
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |

(56) References Cited

U.S. PATENT DOCUMENTS

| | | |
|---|---|---|
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 11,253,255 B2 * | 2/2022 | Eisinger ............ A61B 17/0686 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |

(56) References Cited

U.S. PATENT DOCUMENTS

| | | |
|---|---|---|
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2997908 A1 | 3/2016 |
| EP | 3378411 A1 | 9/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

RELOAD ASSEMBLY WITH KNIFE CARRIER LOCKOUT

CROSS-REFERENCE TO RELATED APPLICATION

This application claims the benefit of and priority to U.S. Provisional Patent Application No. 62/948,400 filed Dec. 16, 2019, the entire disclosure of which is incorporated by reference herein.

FIELD

The disclosure is directed to circular stapling devices and, more particularly, to reload assemblies for circular stapling devices with structure to retain a knife carrier of the reload assembly in a retracted position after the stapling device is fired.

BACKGROUND

Conventional circular stapling devices include an elongate body and a shell or reload assembly that is supported on a distal portion of the elongate body. The reload assembly includes a shell housing, a staple cartridge having a plurality of staples supported on the shell housing, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core or cut tissue.

After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. Removal of the tissue donut under such circumstances has a tendency to pull the knife from within the shell housing. A continuing need exists in the art for a reload assembly that includes improved structure for retaining the knife/knife carrier in a retracted position.

SUMMARY

One aspect of the disclosure is directed to a surgical stapling device including an adaptor assembly and a reload assembly. The adaptor assembly has a proximal end portion and a distal end portion. The reload assembly is supported on the distal end portion of the adaptor assembly and includes a shell housing, an auxiliary detent, a staple cartridge, a staple pusher, a knife carrier, and a knife. The shell housing includes an outer housing portion and an inner housing portion that define an annular cavity. The auxiliary detent is supported within the shell housing. The staple cartridge is secured to the shell housing and supports a plurality of staples. The staple pusher defines a through bore, is supported within the annular cavity of the shell housing, and is movable from a retracted position to an advanced position to eject staples from the staple cartridge. The knife carrier is supported within the through bore of the staple pusher, defines a central bore that receives the inner housing portion of the shell housing, and is movable about the inner housing portion between a retracted position and an advanced position. The knife carrier defines a pocket that receives the auxiliary detent when the knife carrier is in the retracted position to obstruct movement of the knife carrier from the retracted position towards the advanced position. An annular knife is supported on the knife carrier.

Another aspect of the disclosure is directed to a reload assembly including a shell housing, an auxiliary detent, a staple cartridge, a staple pusher, a knife carrier, and an annular knife. The shell housing includes an outer housing portion and an inner housing portion that define an annular cavity. The auxiliary detent is supported within the shell housing. The staple cartridge is secured to the shell housing and supports a plurality of staples. The staple pusher defines a through bore, is supported within the annular cavity, and is movable from a retracted position to an advanced position to eject staples from the staple cartridge. The knife carrier is supported within the through bore of the staple pusher, defines a central bore that receives the inner housing portion of the shell housing, and is movable about the inner housing portion of the shell housing between a retracted position and an advanced position. The knife carrier defines a pocket that receives the auxiliary detent when the knife carrier is in the retracted position to obstruct movement of the knife carrier from the retracted position towards the advanced position. The knife is supported on the knife carrier.

In aspects of the disclosure, the stapling device includes a handle assembly having a proximal end portion and a distal end portion. The proximal end portion of the adaptor assembly is supported on the handle assembly.

In some aspects of the disclosure, the auxiliary detent is longitudinally fixed to the shell housing.

In certain aspects of the disclosure, the auxiliary detent is resilient.

In other aspects of the disclosure, the auxiliary detent is rigid.

In aspects of the disclosure, the knife carrier includes an inner surface that defines the central bore of the knife carrier and supports at least one primary detent, and the inner housing portion of the shell housing includes an outer surface that defines at least one longitudinal recess. The at least one longitudinal recess receives the at least one primary detent. The at least one primary detent has a proximal portion, a distal portion, and an abutment surface that separates the proximal portion of the at least one recess from the distal portion of the at least one recess. The at least one primary detent moves into an interference fit with the abutment surface as the knife carrier is moved from its retracted position towards it advanced position.

In some aspects of the disclosure, a staple actuator is supported within the annular cavity in abutting relation to the staple pusher and is movable from a retracted position to an advanced position to move the staple pusher from its retracted position to its advanced position.

In aspects of the disclosure, the auxiliary detent is in the form of a spring clip.

In some aspects of the disclosure, the knife carrier includes a plurality of resilient longitudinal body portions that define the central bore, wherein each of the longitudinal body portions is spaced from adjacent longitudinal body portions to define longitudinal slots.

In certain aspects of the disclosure, the pocket is defined in adjacent longitudinal body portions of the knife carrier and communicates with a respective one of the longitudinal slots such that the auxiliary detent is aligned with the respective one of the longitudinal slots, wherein the auxiliary detent is movable into the respective one of the longitudinal slots as the knife carrier moves from its retracted position towards its advanced position.

In other aspects of the disclosure, the adaptor assembly includes a knife driver that is adapted to be releasably coupled to the knife carrier.

In aspects of the disclosure, the width of the auxiliary detent is greater than the width of the respective one of the longitudinal slots such that movement of the auxiliary detent through the respective one of the longitudinal slots causes outward deformation of the adjacent longitudinal body portions to urge the knife driver and the knife carrier into more secure engagement.

In some aspects of the disclosure, a bushing is secured to the inner housing portion of the shell housing and the auxiliary detent is supported on the bushing.

Other features of the disclosure will be appreciated from the following description.

BRIEF DESCRIPTION OF THE DRAWINGS

Various aspects of the disclosed reload assembly for a surgical stapling device are described herein below with reference to the drawings, wherein.

DETAILED DESCRIPTION

Figure 1:
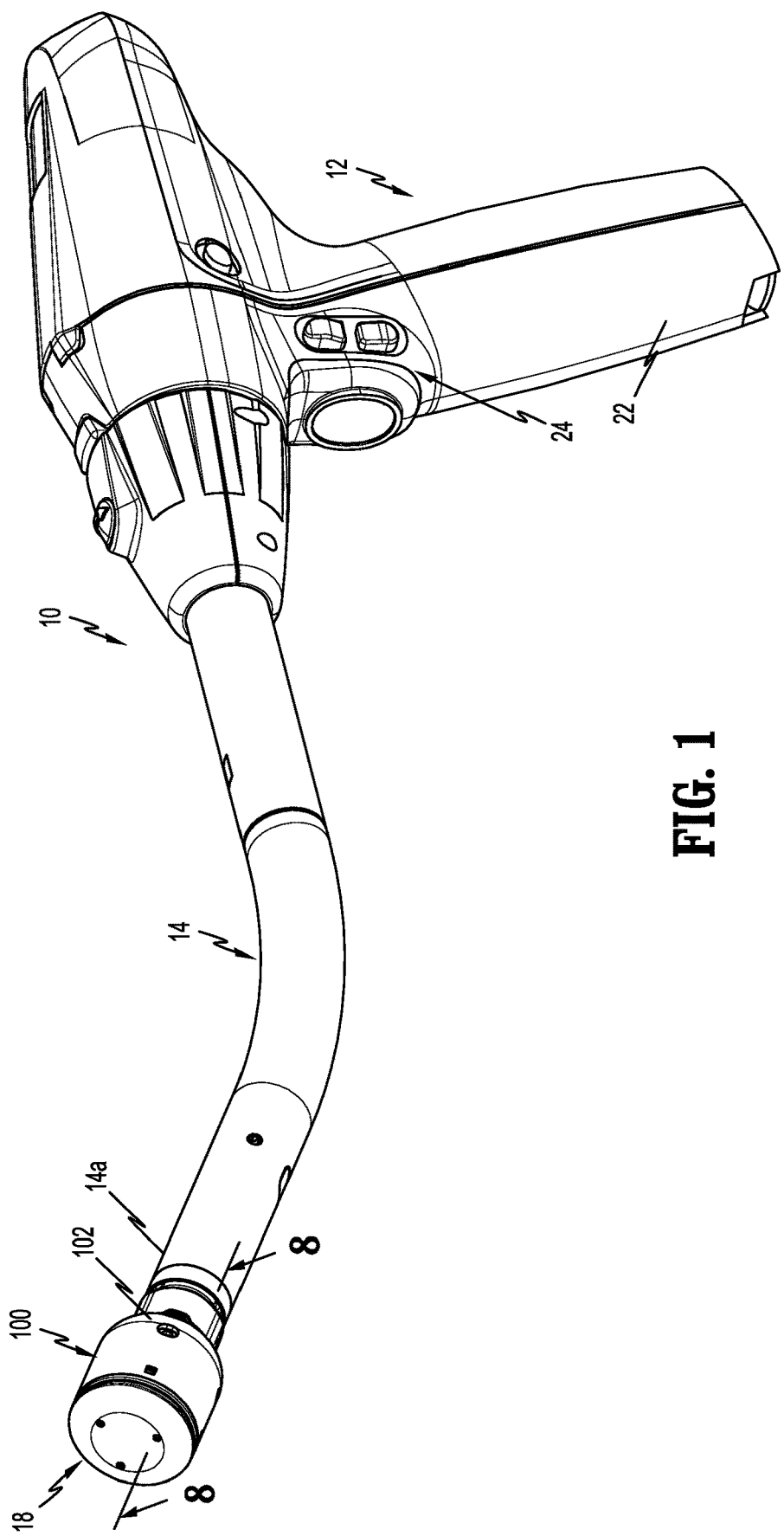
FIG. 1 is a side perspective view of a surgical stapling device including exemplary aspects of the disclosed reload assembly with a tool assembly of the stapling device in a clamped position.

The disclosed reload assembly for a surgical stapling device will now be described in detail with reference to the drawings in which like reference numerals designate identical or corresponding elements in each of the several views. However, it is to be understood that the aspects of the reload assembly disclosed are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
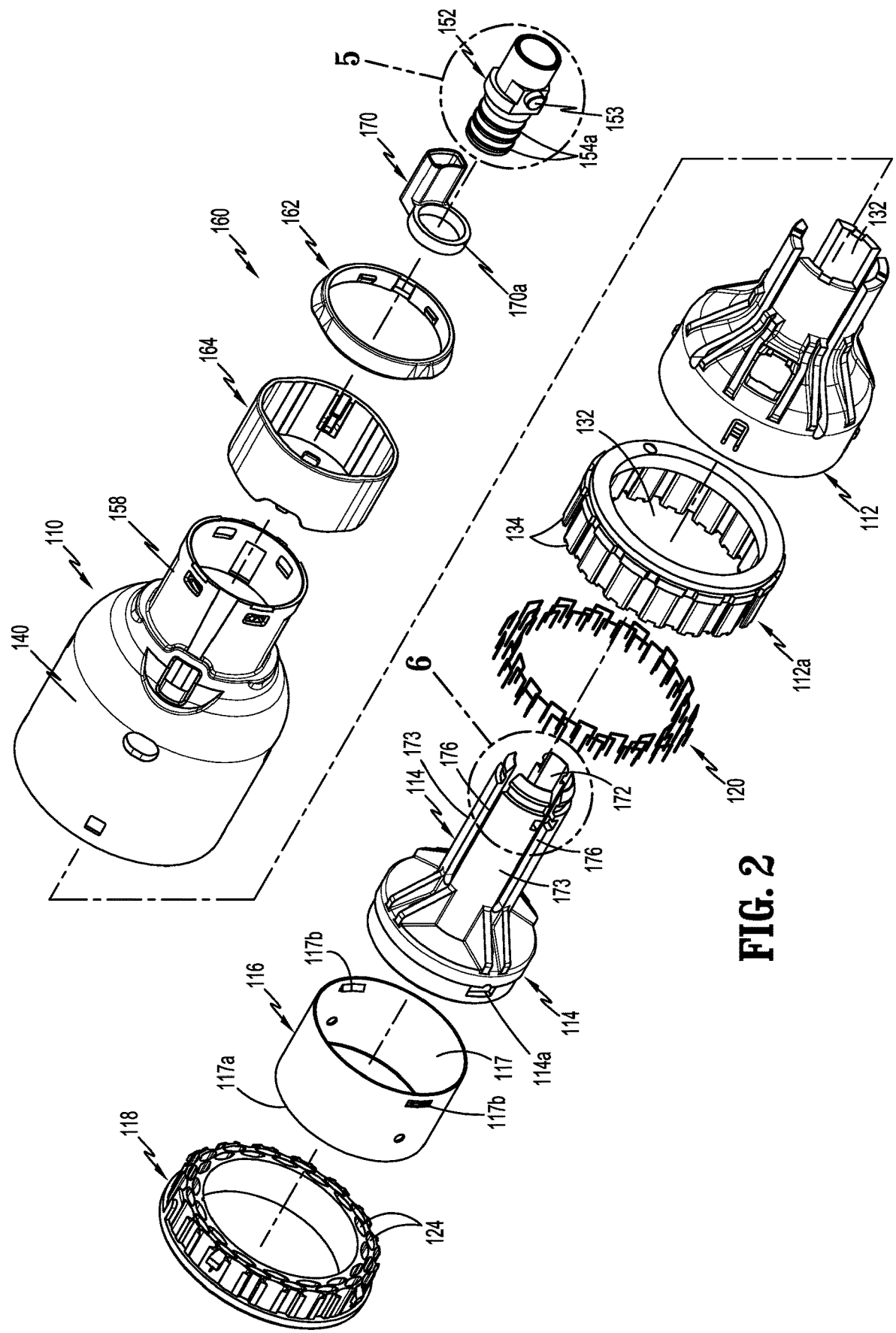
FIG. 2 is an exploded perspective view of the reload assembly shown in FIG. 1.

FIGS. 1 and 2 illustrate a circular stapling device 10 including exemplary aspects of the disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and clamped positions as is known in the art. The reload assembly 100 includes a proximal portion 102 that is releasably coupled to a distal portion 14a of the elongate body 14. In certain aspects of the disclosure, the handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. Nos. 9,055,943, 9,023,014, and U.S. Publication Nos. 2018/0125495, and 2017/0340351. Alternately, it is envisioned that the reload assembly could also be incorporated into a manually powered stapling device such as disclosed in U.S. Pat. No. 7,303,106 (the '106 patent) or a stapling device that is configured for use with a robotic system such as disclosed in U.S. Pat. No. 9,962,159 that does not include a handle assembly.

Figure 3:
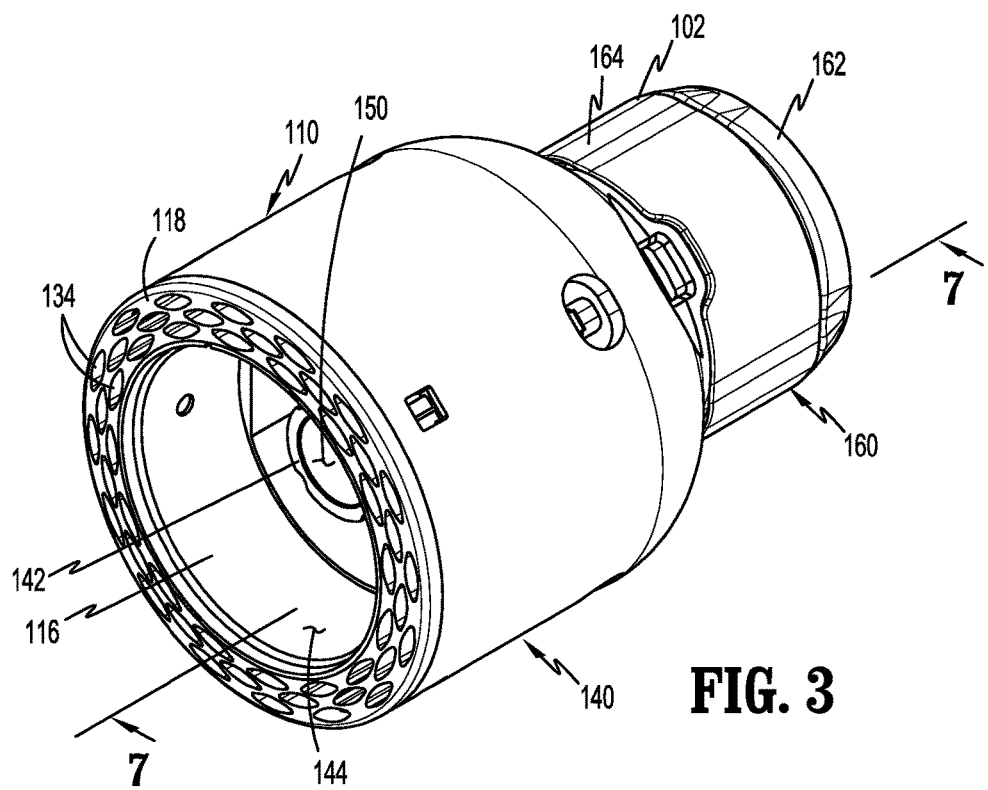
FIG. 3 is a perspective view from the distal end of a shell housing and staple cartridge of the reload assembly shown in FIG. 1.
Figure 4:
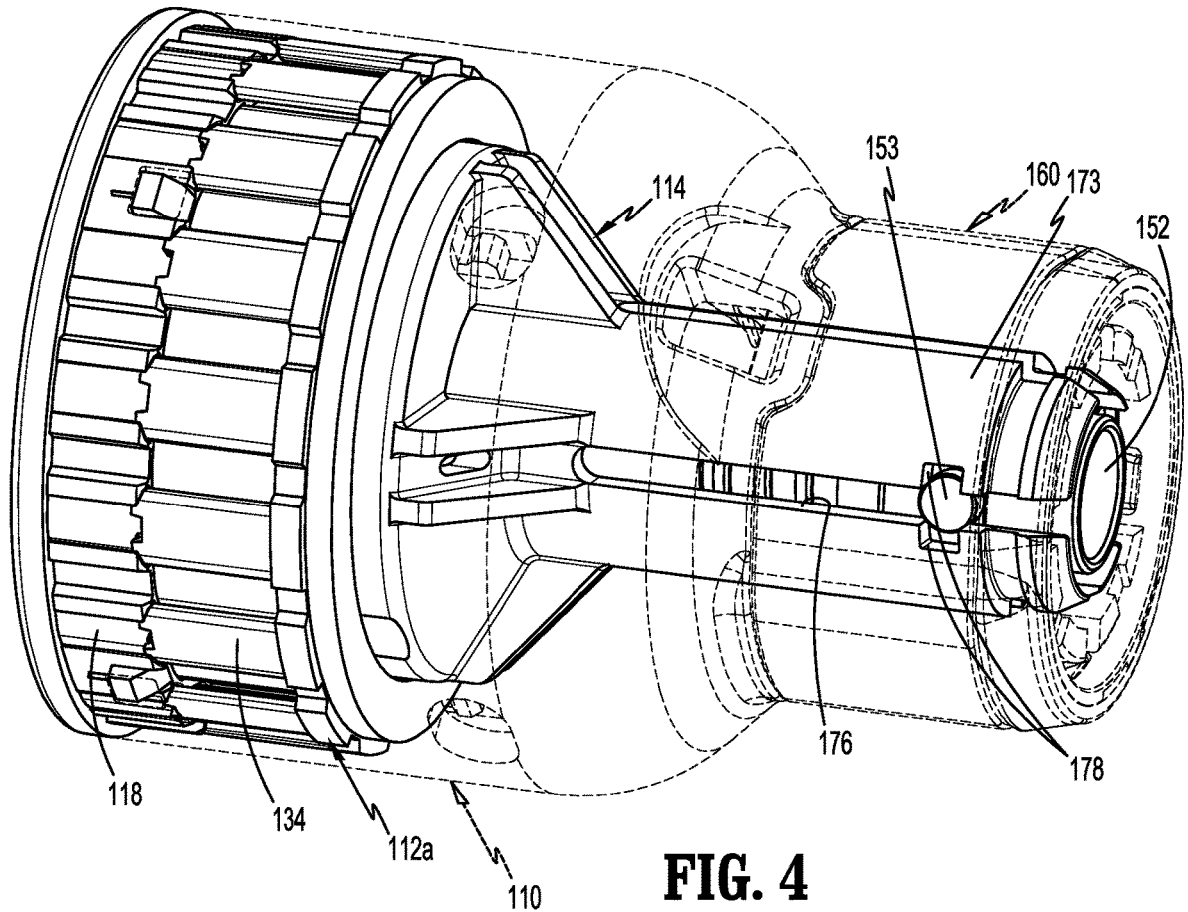
FIG. 4 is a side perspective view of the reload assembly shown in FIG. 1 with the shell housing shown in phantom.
Figure 7:
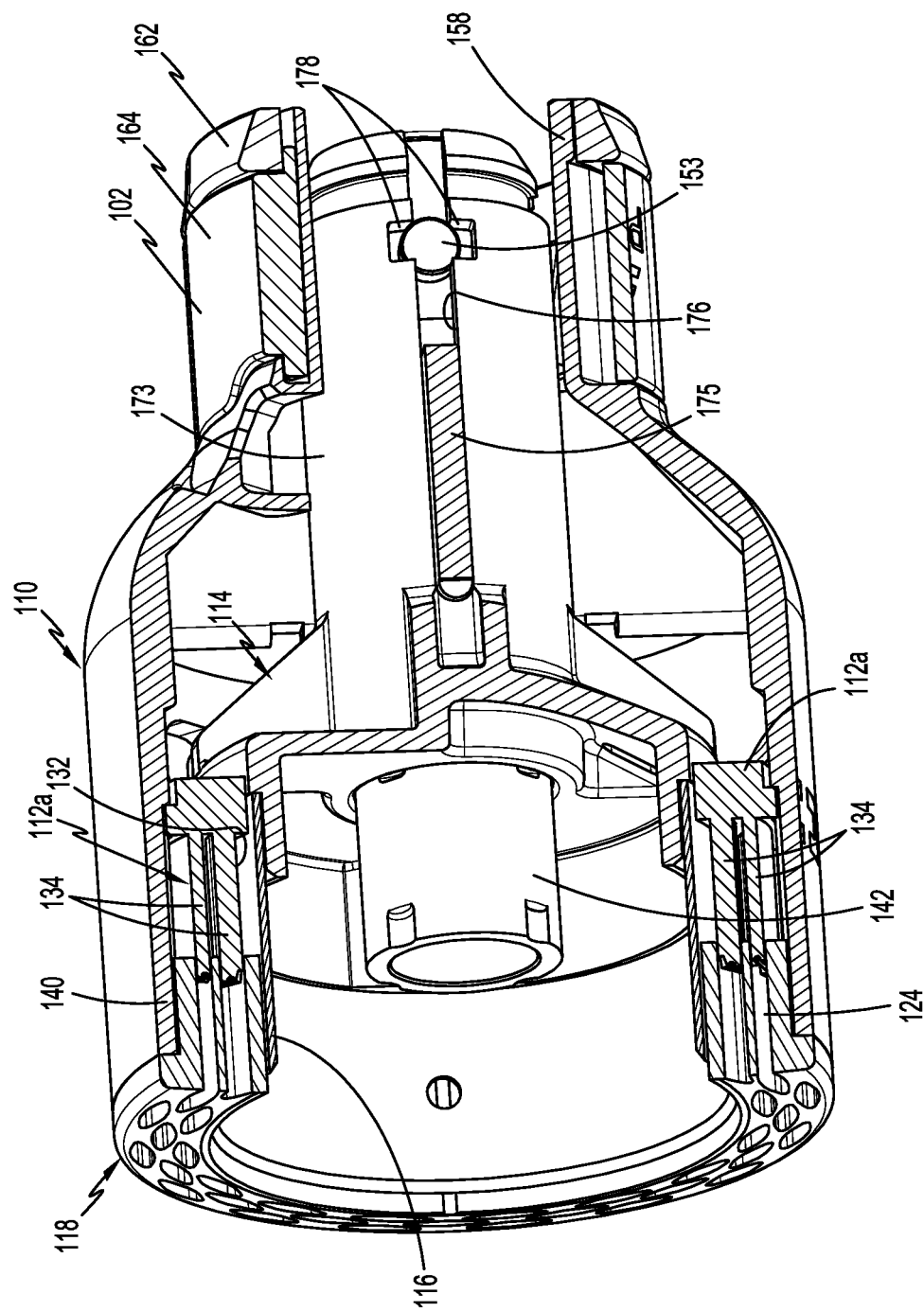
FIG. 7 is a cross-sectional view taken along section line 7-7 of FIG. 3.

FIGS. 2-4 illustrate the reload assembly 100 which includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one staple of the plurality of staples 120. The staple actuator 112 and the staple pushing member 112a together define a longitudinal through bore 132 (FIG. 7). The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 134. Each of the plurality of fingers 134 is received within a respective one of the staple pockets 124 of the staple cartridge 118 and is movable through the respective staple pocket 124 to eject one of the staples 120 from the staple pocket 124 when the staple pushing member 112a is moved from a retracted position to an advanced position within the shell housing 110.

The shell housing 110 includes an outer housing portion 140 and an inner housing portion 142 (FIG. 3) that are spaced from each other to define an annular cavity 144 between the outer and inner housing portions 140 and 142. The staple actuator 112 and the staple pushing member 112a are movable within the annular cavity 144 of the shell housing 110 from retracted positions to advanced positions to eject the staples 120 from the staple cartridge 118.

The annular knife 116 is supported about an outer surface of the knife carrier 114, has a distal cutting edge 117a, and defines a cylindrical cavity 117. In aspects of the disclosure, the annular knife 116 includes inwardly extending tangs 117b (FIG. 2) that are received within pockets 114a defined in an outer surface of the knife carrier 114 to secure the annular knife 116 to the knife carrier 114. The knife carrier 114 and annular knife 116 are positioned within the through bore 132 (FIG. 7) of the staple actuator 112 and are movable from retracted positions to advanced positions to cut tissue positioned radially inward of the staple cartridge 118. It is envisioned that the annular knife 116 can be secured to the knife carrier 114 using a variety of different fastening techniques. It is also envisioned that the annular knife 116 can be secured to an internal surface of the knife carrier 114 rather than to the outer surface of the knife carrier 114.

Figure 5:
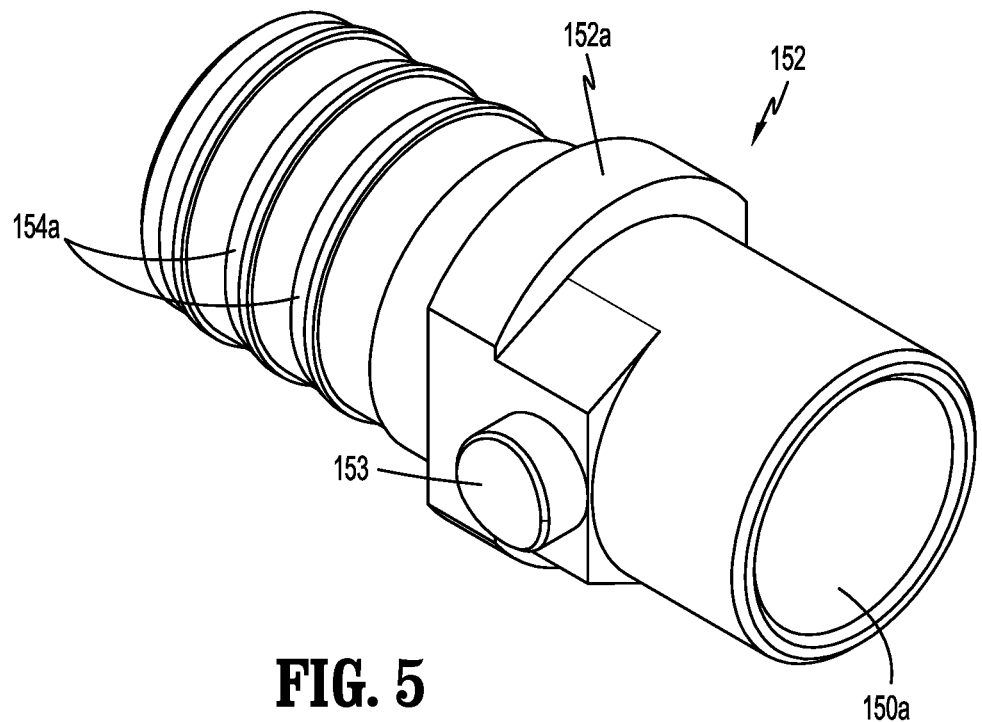
FIG. 5 is an enlarged view of the indicated area of detail shown in FIG. 2.

The inner housing portion 142 of the shell housing 110 defines a through bore 150 (FIG. 3) that receives an anvil shaft (not shown) of the anvil assembly 18. For a more detailed description of an exemplary anvil assembly 18, see, e.g., the '106 patent. The through bore 150 has a proximal portion that receives a bushing 152 best illustrated in FIG. 5. The bushing 152 includes a longitudinally fixed, rigid auxiliary detent 153 that extends radially outward from the bushing 152 and a flange 152a that extends at least partially about the bushing 152. The flange 152a engages the proximal end of the inner housing portion 142 of the shell housing 110 to secure the bushing to the inner housing portion 142. The auxiliary detent 153 is described in further detail below.

The bushing 152 defines a through bore 150a that is coaxial with and forms an extension of the through bore 150 of the inner housing portion 142. The bushing 152 is formed of a high strength material, e.g., metal, to provide added strength to the inner housing portion 142 of the shell housing 110 and includes an annular flange 152a. In some aspects of the disclosure, the bushing 152 includes is distal end 154 that includes one or more retaining rings 154a. The retaining rings 154a are received within the through bore 150 of the inner housing portion 142 of the shell housing 110 and are shaped to inhibit removal of the bushing 152.

The shell housing 110 includes a proximal portion 158 (FIG. 2) that supports a coupling mechanism 160 (FIG. 2) that is operable to releasably couple the reload assembly 100 to the adaptor assembly 14 of the stapling device 10 (FIG. 1). The coupling mechanism 160 allows for removal and replacement of the reload assembly 100 on the elongate body 14 to facilitate reuse of the stapling device 10 and includes a retaining member 162 and a coupling member 164. The coupling member 164 is received about the proximal portion 158 of the shell housing 110 and is configured to engage the distal portion 14a (FIG. 1) of the adaptor assembly 14 to couple the reload assembly 100 to the adaptor assembly 14. The retaining member 162 retains the coupling member 164 in a position about the proximal portion 158 of the shell housing 110. It is envisioned that other coupling mechanisms can be used to secure the reload assembly 100 to the adaptor assembly 14. Alternately, the reload assembly 100 can be non-removably secured to the adaptor assembly 14.

In certain aspects of the disclosure, the reload assembly 100 includes an EPROM (erasable programmable read-only memory) chip holder 170 (FIG. 3) that is supported on the shell housing 110 and is configured to support an EPROM chip. As is known in the art, an EPROM chip communicates with the adaptor assembly 14 to provide information to the adaptor assembly 14 and the handle assembly 12 regarding characteristics of the reload assembly 10. In some aspects of the disclosure, the EPROM chip holder 170 includes a cylindrical collar 170a (FIG. 2) that is received about a distal portion of the bushing 152 within the shell housing 110. The cylindrical collar 170a can be clamped between the proximal end of the inner housing portion 142 of the shell housing 110 and the flange 152a of the bushing 152 to secure the EPROM chip holder within the shell housing 110.

Figure 7A:
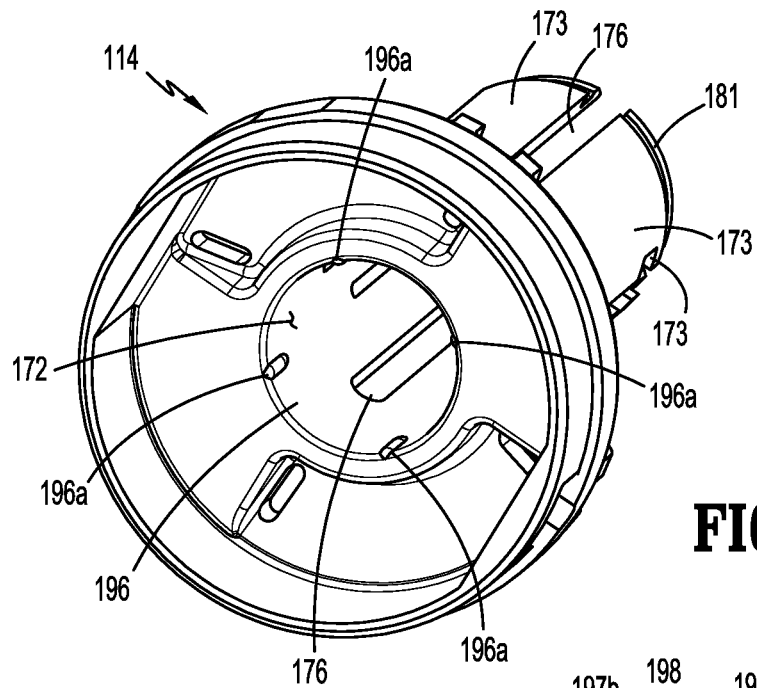
FIG. 7A is a perspective view from the distal end of the knife carrier of the reload assembly shown in FIG. 2.
Figure 10:
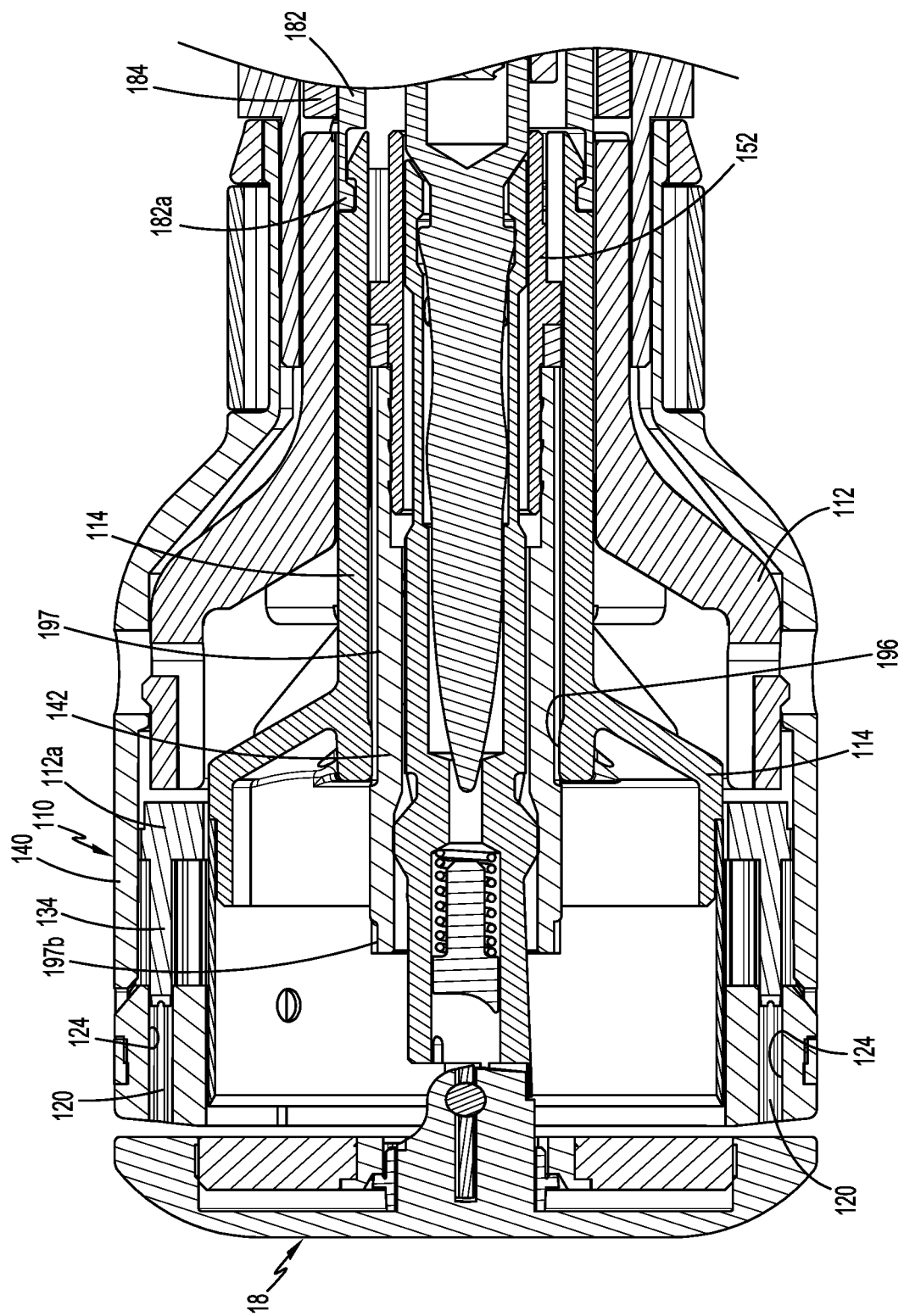
FIG. 10 is a side cross-sectional view of the tool assembly of the surgical stapling device shown in FIG. 1 with the tool assembly in the clamped, pre-fired position.
Figure 11:
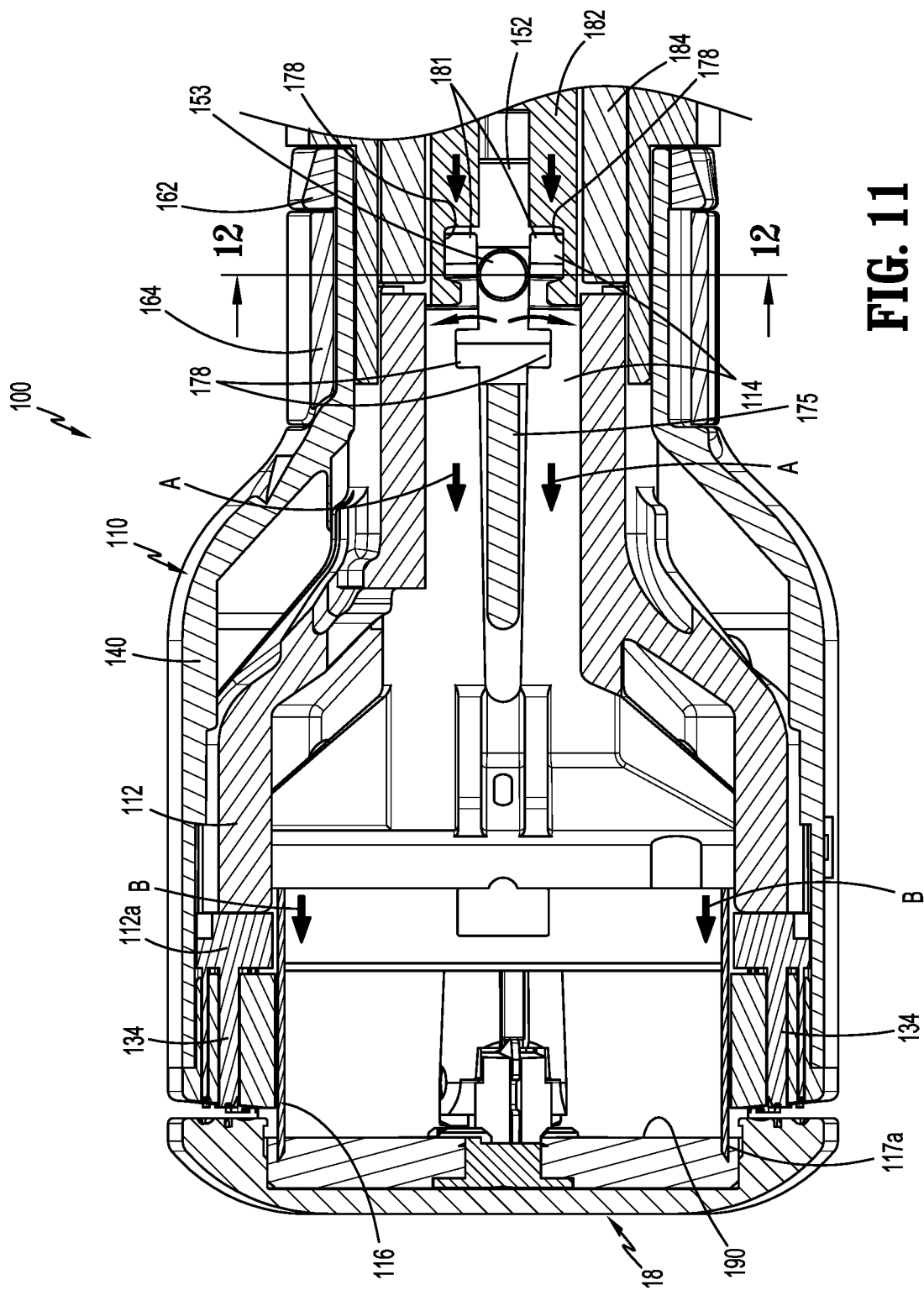
FIG. 11 is a side cross-sectional view of the tool assembly of the surgical stapling device shown in FIG. 1 with the tool assembly in the clamped, and fired position and the knife carrier in the advanced position.

The knife carrier 114 (FIG. 2) includes spaced resilient longitudinal body portions 173 that are spaced from each other and together define a central bore 172 (FIG. 7A). The central bore 172 of the knife carrier 114 is slidable about the inner housing portion 142 (FIG. 3) of the shell housing 110 such that the knife carrier 114 is movable about the inner housing portion 142 between a retracted position (FIG. 10) and an advanced position (FIG. 11). Each of the longitudinal body portions 173 of the knife carrier 114 is formed of a resilient material and is spaced from adjacent body portions 173 to define slots 176 between the adjacent body portions 173. The slots 176 receive guide portions 175 (FIG. 7B) of the shell housing 110 to limit the knife carrier 114 to longitudinal movement within the shell housing 110. The guide portions 175 extend between the inner and outer housing portions 142, 140 of the shell housing 110. At least one of the longitudinal body portions 173 defines a pocket 178 that communicates with one of the slots 176. In certain aspects of the disclosure, two of the longitudinal body portions 173 define pockets 178 that are positioned in longitudinal alignment with each other on opposite sides of a respective slot 176 to define the pocket 178. The pocket 178 receives the auxiliary detent 153 of the bushing 152 when the knife carrier 114 is in its retracted position.

Figure 7B:
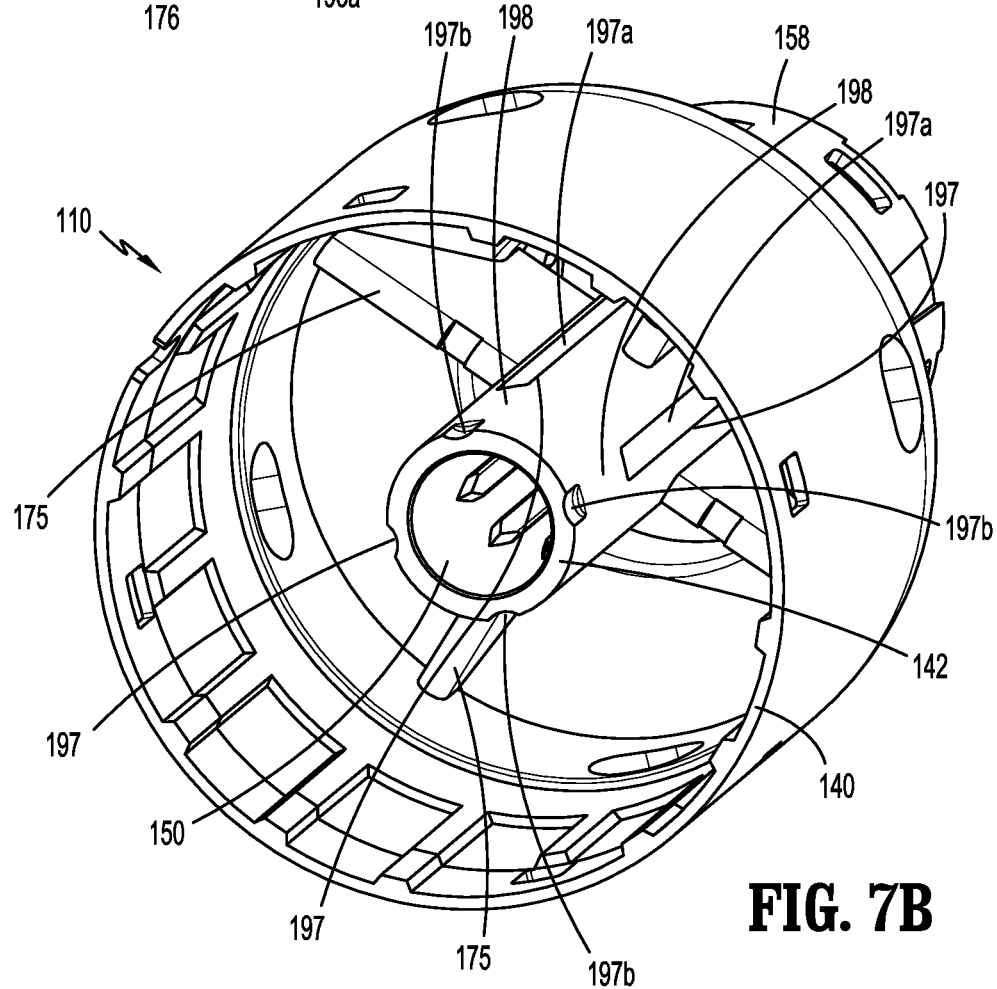
FIG. 7B is a perspective view from the distal end of the shell housing of the reload assembly shown in FIG. 2.
Figure 8:
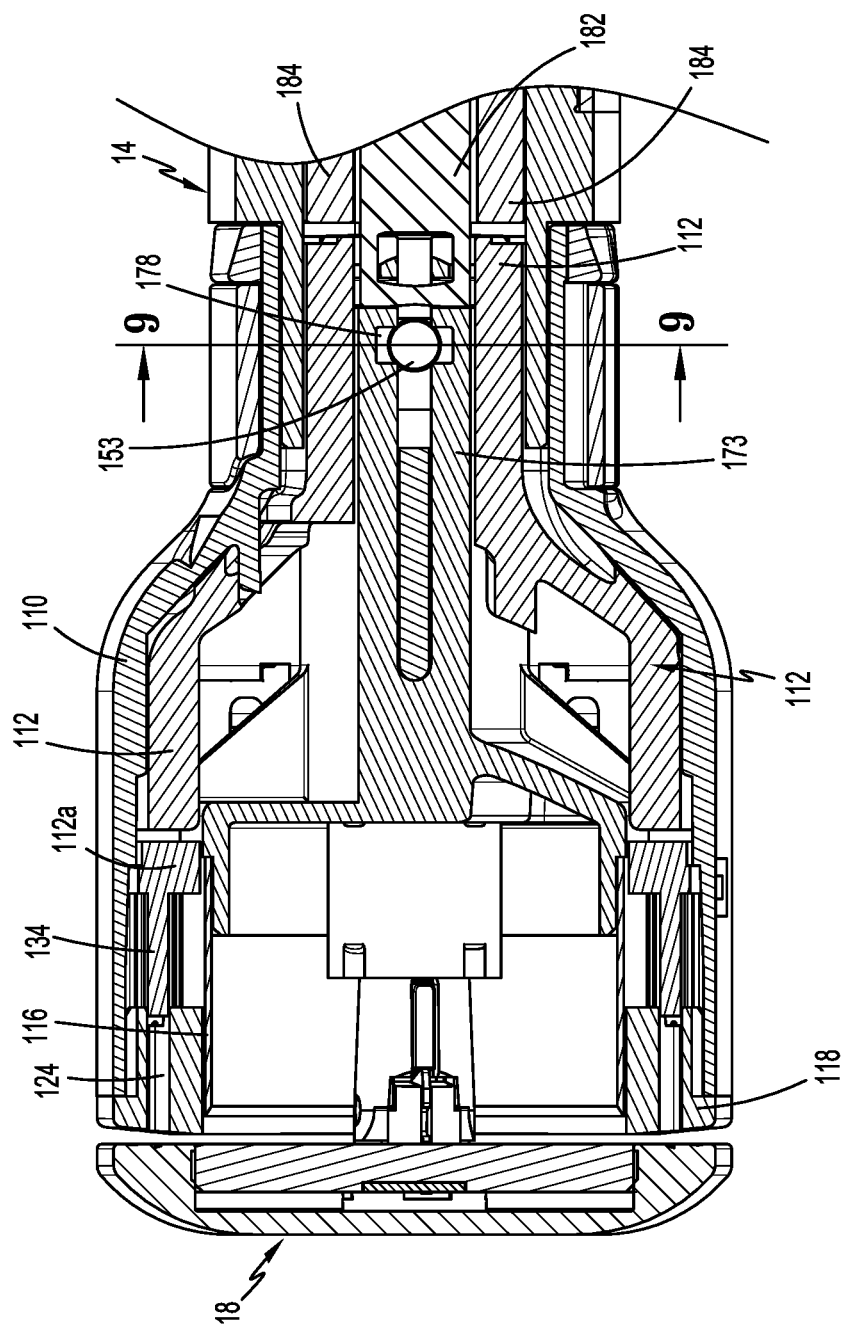
FIG. 8 is a cross-sectional view taken along section line 8-8 of FIG. 1.
Figure 9:
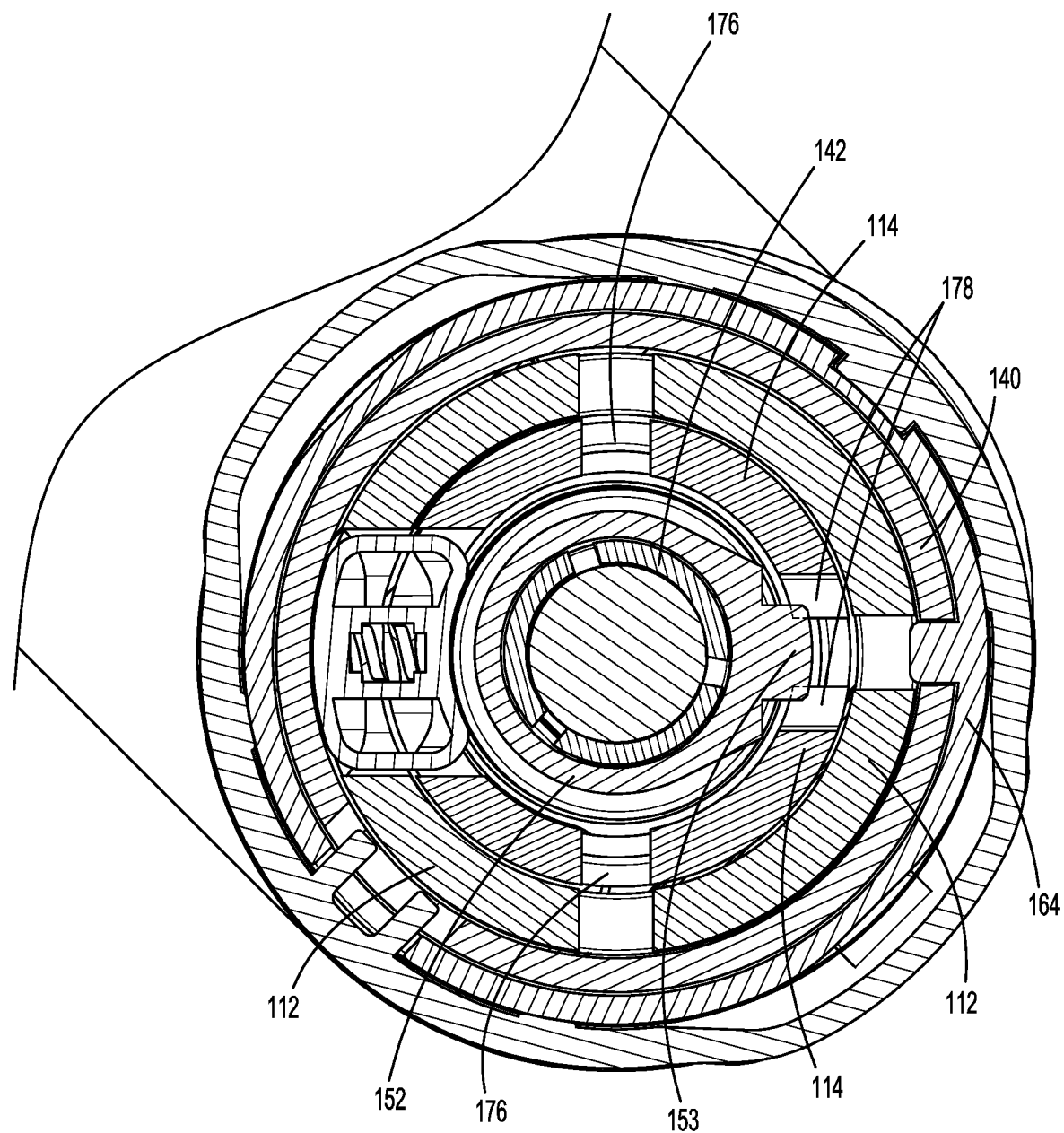
FIG. 9 is a cross-sectional view taken along section line 9-9 of FIG. 8.

FIGS. 7A and 7B illustrate perspective views from the distal end of the knife carrier 114 and the shell housing 110. As illustrated, the longitudinal body portions 173 of the knife carrier 114 include an inner surface 196 that defines the central bore 172 of the knife carrier 114 and supports one or more primary detents 196a. The primary detents 196a, of which four are shown, are supported about the periphery of the inner surface 196 of the knife carrier 114. In certain aspects of the disclosure, the primary detents 196a are secured to the inner surface 196 of the knife carrier 114, although it is envisioned that the primary detents can be integrally formed with the knife carrier 114.

The outer surface of the inner housing portion 142 includes one or more elongated longitudinal recesses 197. The recesses 197, of which four are shown, each receive a respective one of the primary detents 196a. Each of the recesses 197 include a proximal portion 197a and a distal portion 197b that are separated by an abutment surface 198. When the knife carrier 114 is in its retracted position, the primary detents 196a are received in the proximal portion 197a of the recesses 197 formed in the inner housing portion 142 of the knife carrier 110 at a positon adjacent the abutment surface 198. When the knife carrier 114 is advanced from its retracted position towards its advanced position, the primary detents 196a are forced to pass over the abutment surface 198 and pass into the distal portion 197b of the recesses 197. As the detents 196a pass over the abutment surface 198, the detents 196a are in an interference fit with the abutment surface 198.

Figure 6:
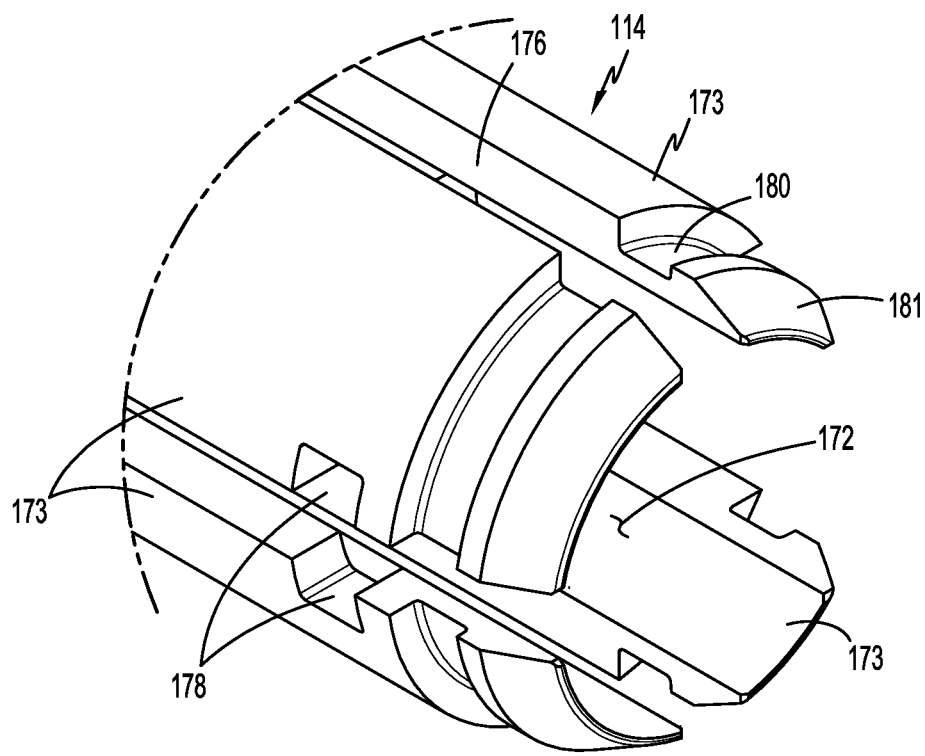
FIG. 6 is an enlarged view of the indicated area of detail shown in FIG. 2.

FIG. 6 illustrates a proximal portion of the knife carrier 114 which defines an outwardly facing annular recess or channel 180 that extends about each of the longitudinal body portions 173. The channel 180 is defined on its proximal end by a tapered abutment 181 and is configured to releasably receive an inwardly extending engagement portion 182a (FIG. 10) of a knife band or driver 182 to facilitate movement of the knife driver 114 between its retracted and advanced positions. The longitudinal body portions 173 of the knife carrier 114 are formed of a resilient material to allow the longitudinal body portions 173 to flex inwardly and outwardly into and out of engagement with the knife driver 182. This structure facilitates removal and replacement of the reload assembly 100 in relation to the elongate body 114 of the stapling device 10.

FIGS. 7-10 illustrate the reload assembly in a clamped, pre-fired position. In this position, the staple actuator 112 (FIG. 8), the staple pushing member 112a, the knife carrier 114, and the annular knife 116 are in their retracted positions. When the knife carrier 114 is in its retracted position, the annular knife 116 is recessed within the staple cartridge 118 and the auxiliary detent 153 of the bushing 152 is received within the pocket 178 of the longitudinal body portions 172 of the knife carrier 114. In this position, the auxiliary detent 153 is aligned with a respective one of the slots 176 defined between adjacent body portions 173 of the knife carrier 114. In addition, as described above, when the knife carrier 114 is in its retracted position, the primary detents 196a are received in the proximal portion 197a of the recesses 197 in the inner housing portion 142 of the shell housing 110 at a positon adjacent the abutment surface 198.

When the staple actuator 112 is in its retracted position, the staple pushing member 112a is also in its retracted position with the fingers 134 of the staple pushing member 112a aligned with and positioned proximally of the staples 120 supported within the staple pockets 124. Although not described in detail herein, the adapter assembly 14 includes a staple driver 184 and the knife driver 182. As described above, the knife driver 182 is coupled to the knife carrier 114 and is longitudinally movable to move the knife carrier 114 between its advanced and retracted positions. Similarly, the staple driver 184 is coupled to the staple actuator 112 and is longitudinally movable to move the staple actuator 112 between its retracted and advanced positions.

Figure 12:
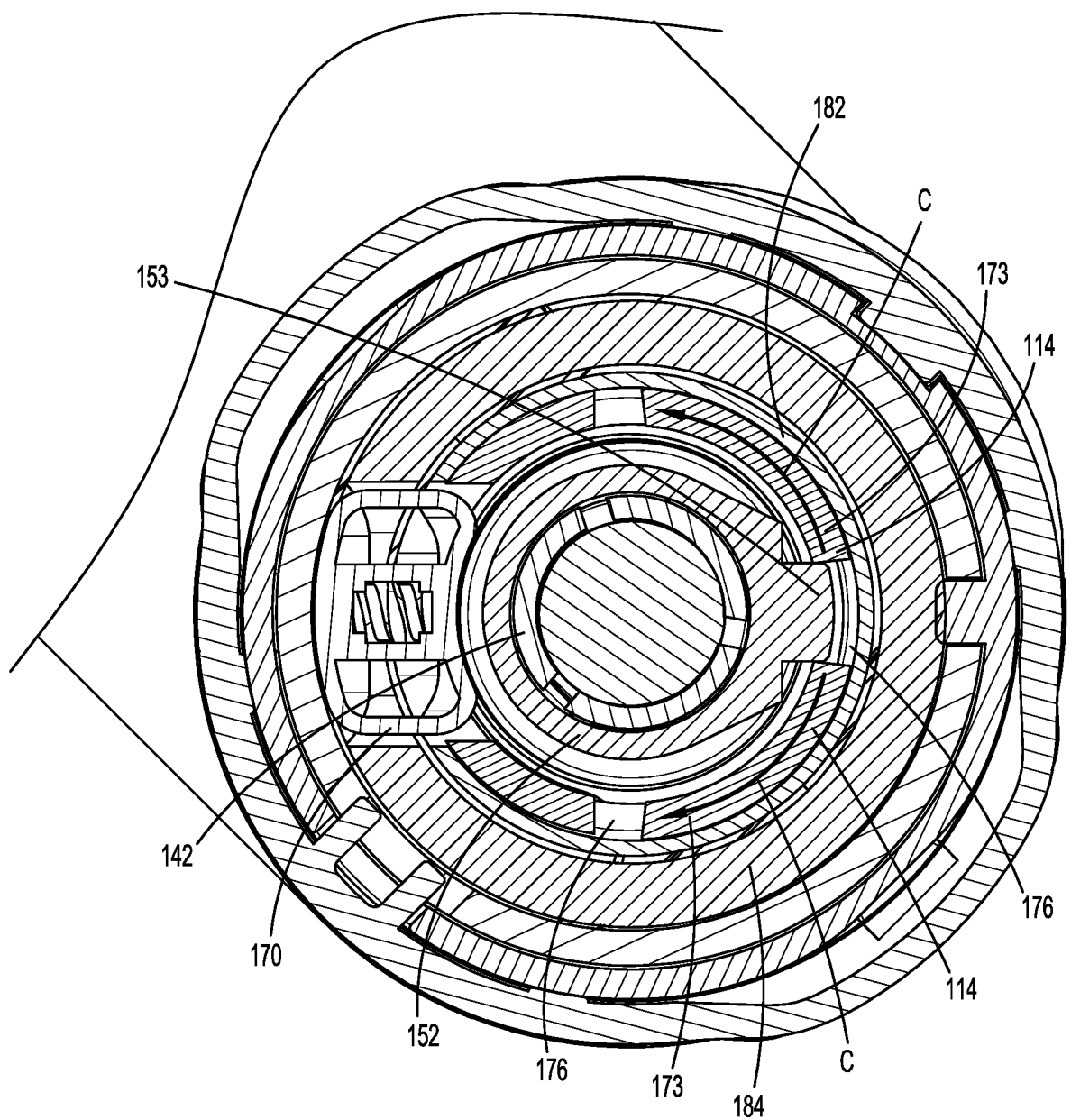
FIG. 12 is a cross-sectional view taken along section line 12-12 of FIG. 11.

FIGS. 11-12 illustrate the reload assembly 100 in a clamped position with the knife carrier 114 and the staple actuator 112 moving towards their fully advanced fired positions. When the stapling device 10 (FIG. 1) is actuated by depressing actuation buttons 24 on the handle assembly 12 (FIG. 1), the knife driver 182 and the staple driver 184 are advanced within the elongate body 14 to advance the knife carrier 114 and the staple actuator 112 within the shell housing 110. As the staple driver 184 and the knife driver 182 are advanced in the direction indicated by arrows "A" in FIG. 11, the staple actuator 112 and the knife carrier 114, which are coupled to the staple driver 184 and the knife driver 182, respectively, are advanced from their retracted positions (FIG. 10) towards their advanced positions (FIG. 11). It is envisioned that the staple driver 184 is advanced before or simultaneously with the knife driver 182 to ensure that tissue is sutured or stapled prior to being cut. As described above, the staple actuator 112 is in abutting relation to the staple pushing member 112a. As such, when the staple actuator 112 is advanced, the staple pushing member 112a is advanced to move the fingers 134 of the staple pushing member 112a through the staple pockets 124 in the cartridge 118 to eject the staples 120 from the cartridge 118. When the knife driver 182 is advanced, the knife carrier 114 is advanced to advance the annular knife 116 in the direction indicated by arrows "B" in FIG. 11 into engagement with a cut ring assembly 190 (FIG. 11) of the anvil assembly 18 to cut tissue clamped between the anvil assembly 18 and the cartridge 118.

When the knife carrier 114 is advanced from its retracted position towards its advanced position, the primary detents 196a are forced to pass over the abutment surface 198 and pass into the distal portion 197b of the recesses 197. As the detents 196a pass over the abutment surface 198, the detents 196a are in an interference fit with the abutment surface 198. The interaction between the primary detents 196a and the recesses 197 increases the knife carrier retention force within the reload assembly 100 as described in further detail below.

The bushing 152 and the auxiliary detent 153 are fixedly supported within the shell housing 110. When the knife carrier 114 is advanced within the shell housing 110 from its retracted position towards its advanced position, the longitudinal body portions 173 move in relation to the auxiliary detent 153 to remove auxiliary detent 153 from a position within the pocket 178 of the longitudinal body portions 173 to a position within one of the slots 176. The width (or diameter) of the auxiliary detent 153 is greater than the width of the slots 176. As such, when the auxiliary detent 153 is positioned within one of the slots 176 defined by the longitudinal body portions 173 of the knife carrier 114, as the knife carrier 114 moves within the shell housing 110 from its retracted position to its advanced position, the adjacent longitudinal body portions 173 that define the slot 176 are biased outwardly in the direction indicated by arrows "C" in FIG. 11. As shown, when the longitudinal body portions 173 are biased outwardly, the tapered abutment 181 of the knife driver 114 and the engagement portion 182a of the knife driver 182 are urged into tight engagement to prevent separation of the knife driver 182 and the knife carrier 114.

Figure 13:
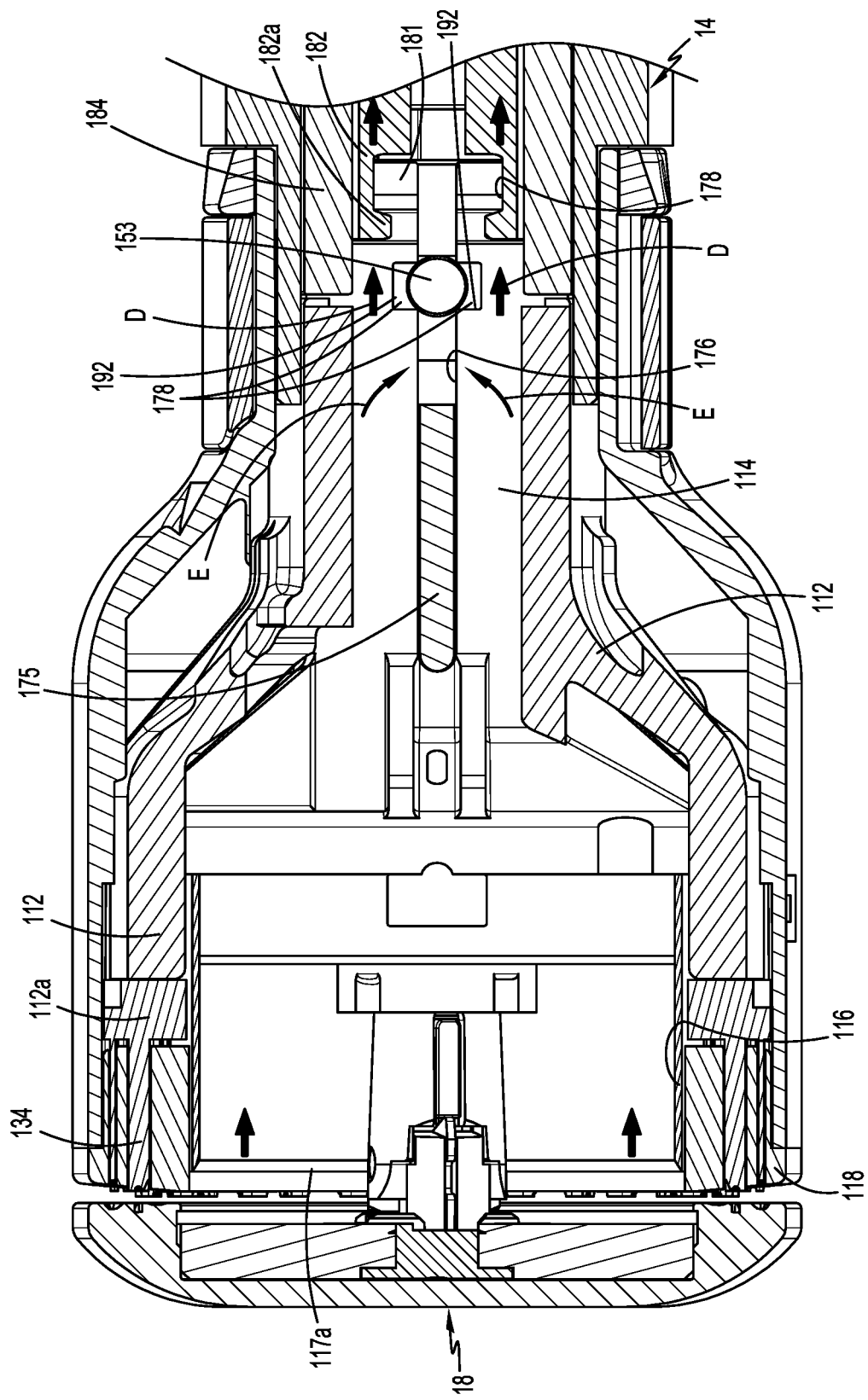
FIG. 13 is a side cross-sectional view of the tool assembly of the surgical stapling device shown in FIG. 1 with the tool assembly in the clamped, and fired position and the knife carrier in the retracted position.
Figure 14:
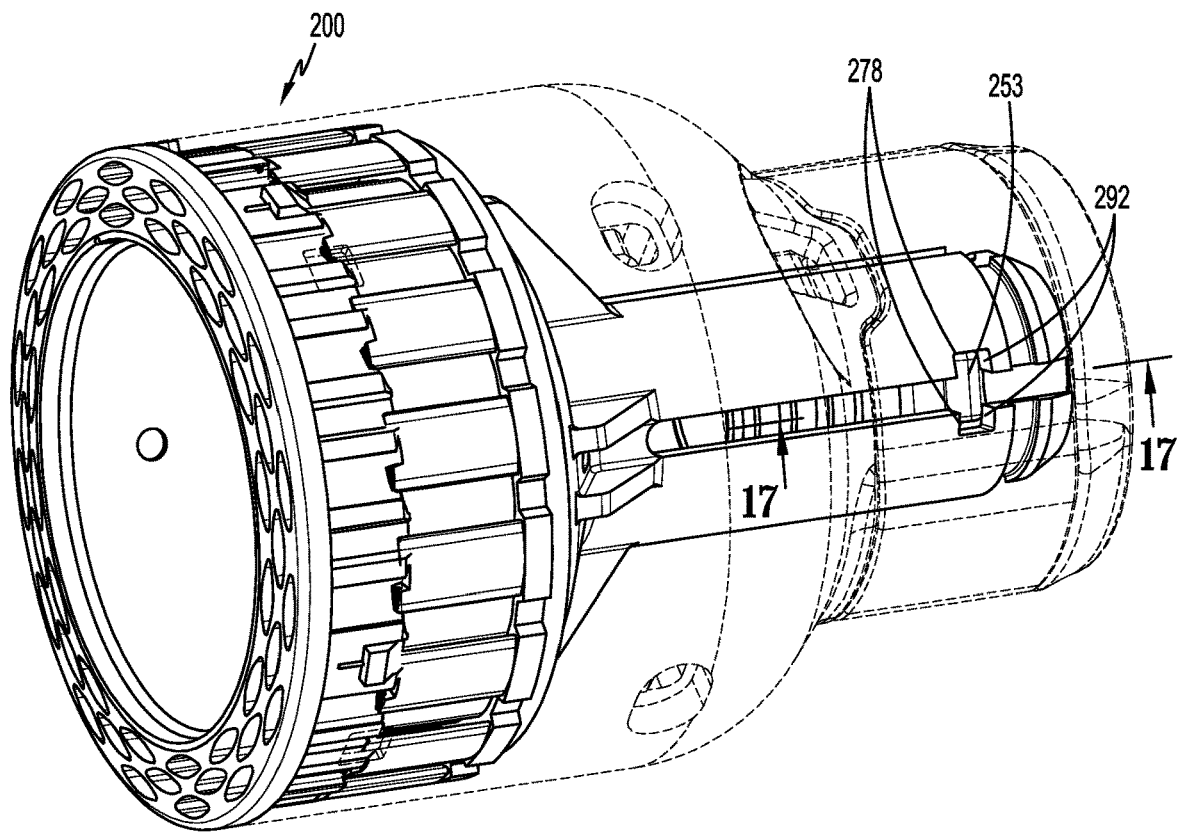
FIG. 14 is a side perspective view of the reload assembly shown in FIG. 1 with the shell housing shown in phantom and including alternative aspects of the present disclosure.
Figure 15:
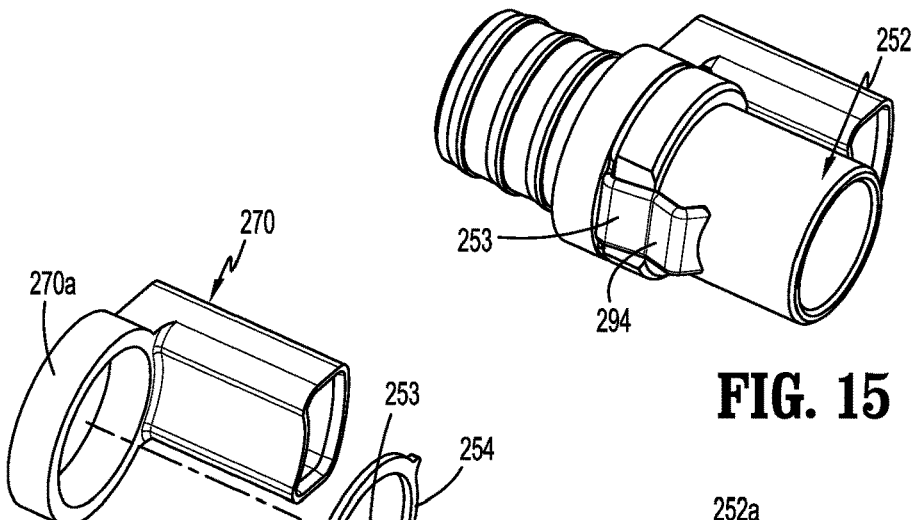
FIG. 15 is a side perspective assembled view of the bushing, EPROM chip holder, and stationary spring clip of the reload assembly shown in FIG. 14.
Figure 16:
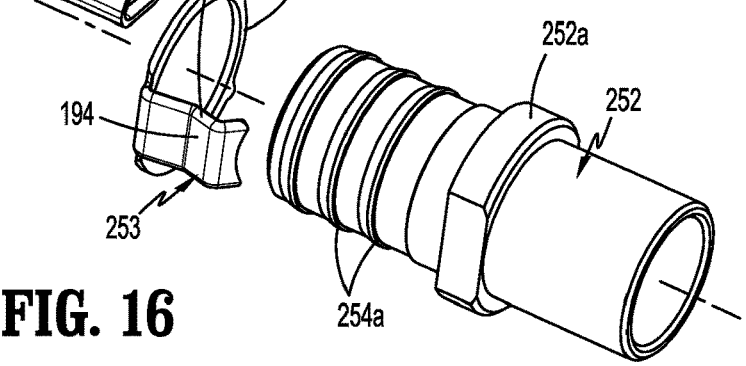
FIG. 16 is a side perspective exploded view of the bushing, EPROM chip holder, and stationary spring clip of the reload assembly shown in FIG. 14.
Figure 17:
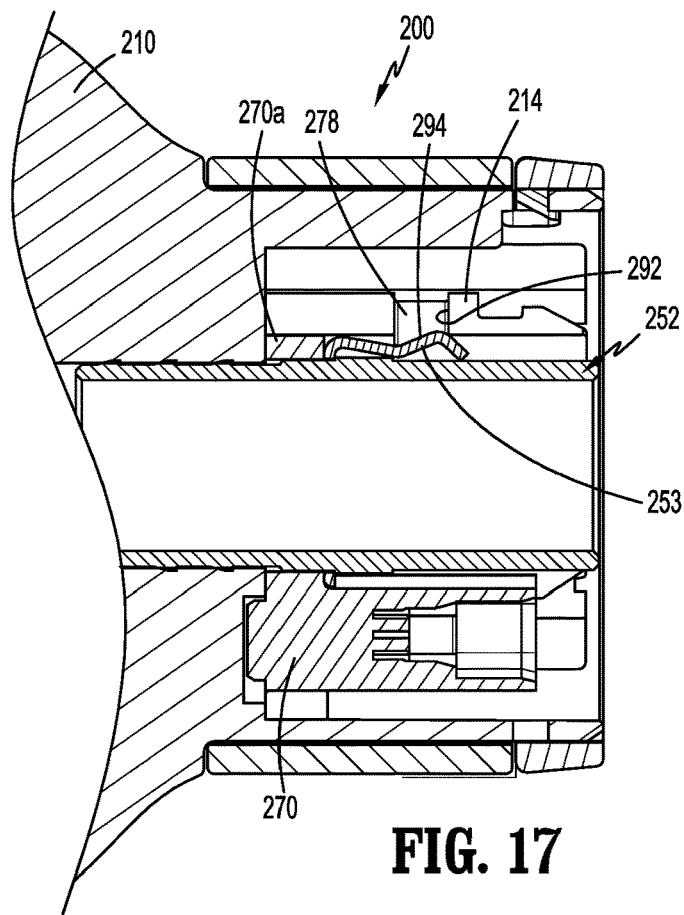
FIG. 17 is a side cross-sectional view of the reload assembly shown in FIG. 14 with the with the knife carrier in the retracted position.
Figure 18:
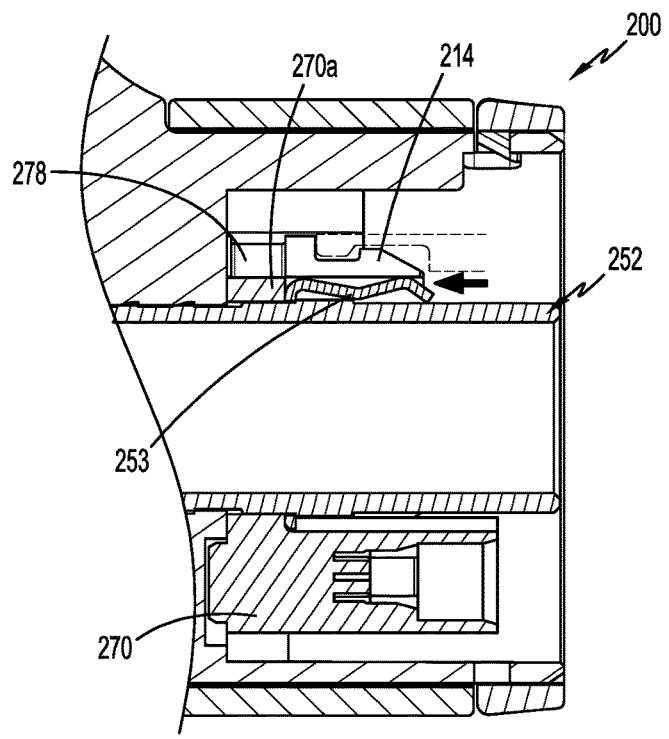
FIG. 18 is a side cross-sectional view of the reload assembly shown in FIG. 14 with the knife carrier in the advanced position.

FIG. 13 illustrates the reload assembly 100 in a fired and clamped position with the knife carrier 114 and the staple actuator 112 returned in the direction indicated by arrows "D" to their retracted positions. When the knife carrier 114 is returned to its retracted position after firing of the stapling device 10 (FIG. 1), the auxiliary detent 153 moves through the longitudinal slot 176 and returns a position within the pocket 178. Engagement between the auxiliary detent 153 and the longitudinal body portions 173 of the knife carrier 114 maintain engagement between the knife driver 182 and the knife carrier 114 until the auxiliary detent passes back into the pocket 178. When the auxiliary detent 153 is received within the pocket 178, the longitudinal body portions 173 move inwardly in the direction of arrows "E" to reduce the engagement force between the tapered abutments 181 of the knife carrier 114 and the engagement portion 182a of the knife driver 182. As the knife carrier 114 is retracted, the annular knife 116 is retracted to a position recessed within the staple cartridge 118 to shield the cutting edge 117a of the annular knife 116 from the clinician. The auxiliary detent 153 obstructs further advancement of the knife carrier 114. More particularly, the auxiliary detent 153 is positioned to engage inner walls 192 that define the pocket 178 to obstruct readvancement off the knife carrier 114 and, thus readvancement of the annular knife 116 from its shielded position within the staple cartridge 118.

When the knife carrier 114 is returned to its retracted position, the primary detents 196a move proximally from the distal portion 197b of the recesses 197, across the abutment surface 198, and back into the proximal portion 197a of the recesses 197. When the detents 196a are received in the proximal portion 197a of the recesses 197, engagement between the detents 196a and the abutment surface 198 increases the retention force on the knife carrier 114 to minimize any likelihood of readvancement of the knife carrier 114.

FIGS. 14-18 illustrate a reload assembly shown generally as reload assembly 200 including additional aspects of the disclosure. The reload assembly 200 is substantially similar to reload assembly 100 with the exception that the auxiliary detent 153 (FIG. 2) of the bushing 252 has been replaced by a longitudinally fixed, resilient auxiliary detent, e.g., a spring clip 253. In certain aspects of the disclosure, the resilient auxiliary detent 253 is secured to a support ring 254 that is received about the about the bushing 252. In certain aspects of the disclosure, the support ring 254 is secured to the bushing 252 and compressed between the cylindrical collar 270a of the EPROM holder 270 and the flange 252a (FIG. 16) of the bushing 252. The flange 252a may include a flat 252b that supports the spring clip 253. It is envisioned that the resilient auxiliary detent 253 can be secured to the bushing 252 in a variety different manners using a variety of different techniques.

When the knife carrier 214 is in a retracted position (FIG. 14), the resilient auxiliary detent 253 is received within the pocket 278 of the knife carrier 214. In certain aspects of the disclosure, the resilient auxiliary detent 253 includes a tapered, distally facing engagement surface 294 that is aligned with the inner walls 292 that define the pocket 278 in the longitudinally extending body portions 273 of the knife carrier 214. When the knife carrier 214 is moved from its retracted position (FIG. 17) towards its advanced position, the resilient auxiliary detent 253 is deformed inwardly by the inner walls 292 of the knife carrier 214 as the knife carrier 214 drives over the resilient auxiliary detent 253. In its deformed state (FIG. 18), the resilient auxiliary detent 253 applies an outwardly directed force onto the longitudinally extending body portion 273 of the knife carrier 214 to urge the knife carrier 214 into more secure engagement with the knife driver 182 (FIG. 11). After the reload 200 is fired and the knife carrier 214 is returned to its retracted position (FIG. 17), the resilient auxiliary detent 253 returns to a position located within the pocket 278 to obstruct further advancement of the knife carrier 214.

The resilient auxiliary detent 253 of the reload assembly 200 and the fixed auxiliary detent 153 of the reload assembly 100 in combination with the primary detents 196a on the knife carrier 114 and 214 and recesses 197 on the shell housing 110, 210, provide the disclosed reload assemblies with additional retention structure to minimize the likelihood of readvancement of the knife carrier and annular knife to improve safety for clinicians.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an adaptor assembly having a proximal end portion and a distal end portion; and
a reload assembly supported on the distal end portion of the adaptor assembly, the reload assembly including:
a shell housing including an outer housing portion and an inner housing portion, the inner and outer housing portions defining an annular cavity;
an auxiliary detent supported within the shell housing and longitudinally fixed to the shell housing;
a staple cartridge secured to the shell housing and supporting a plurality of staples;
a staple pusher defining a through bore, the staple pusher supported within the annular cavity and movable from a retracted position to an advanced position to eject the plurality of staples from the staple cartridge;
a knife carrier supported within the through bore of the staple pusher and defining a central bore that receives the inner housing portion of the shell housing, the knife carrier movable about the inner housing portion between a retracted position and an advanced position, the knife carrier defining a pocket that receives the auxiliary detent when the knife carrier is in the retracted position to obstruct movement of the knife carrier from the retracted position towards the advanced position; and
an annular knife supported on the knife carrier.

2. The surgical stapling device of claim 1, further including a handle assembly, the proximal end portion of the adaptor assembly being supported on the handle assembly.

3. The surgical stapling device of claim 1, wherein the auxiliary detent is resilient.

4. The surgical stapling device of claim 3, wherein the auxiliary detent is in the form of a spring clip.

5. The surgical stapling device of claim 1, wherein the auxiliary detent is rigid.

6. The surgical stapling device of claim 1, wherein the knife carrier includes an inner surface that defines the central bore of the knife carrier, the inner surface of the knife carrier supporting at least one primary detent, the inner housing portion of the shell housing including an outer surface that defines at least one longitudinal recess that receives the at least one primary detent, the at least one primary detent having a proximal portion, a distal portion, and an abutment surface that separates the proximal portion of the at least one recess from the distal portion of the at least one recess, wherein the at least one primary detent moves into an interference fit with the abutment surface as the knife carrier is moved from its retracted position towards it advanced position.

7. The surgical stapling device of claim 1, wherein the knife carrier includes a plurality of resilient longitudinal body portions that define the central bore, each of the longitudinal body portions being spaced from adjacent longitudinal body portions to define longitudinal slots.

8. The surgical stapling device of claim 1, wherein the pocket is defined in adjacent longitudinal body portions of the knife carrier and communicates with a respective one of the longitudinal slots such that the auxiliary detent is aligned with the respective one of the longitudinal slots, the auxiliary detent being movable into the respective one of the longitudinal slots as the knife carrier moves from its retracted position towards its advanced position.

9. The surgical stapling device of claim 8, wherein the adaptor assembly includes a knife driver that is adapted to be releasably coupled to the knife carrier.

10. The surgical stapling device of claim 9, wherein the width of the auxiliary detent is greater than the width of the respective one of the longitudinal slots such that movement of the auxiliary detent through the at least one of the longitudinal slots causes deformation of the adjacent longitudinal body portions to urge the knife driver and the knife carrier into more secure engagement.

11. The surgical stapling device of claim 1, further including a bushing secured to the inner housing portion of the shell housing, wherein the auxiliary detent is supported on the bushing.

12. A reload assembly comprising:
a shell housing including an outer housing portion and an inner housing portion, the inner and outer housing portions defining an annular cavity;
an auxiliary detent supported within the shell housing and longitudinally fixed to the shell housing;
a staple cartridge secured to the shell housing and supporting a plurality of staples;
a staple pusher defining a through bore, the staple pusher supported within the annular cavity and movable from a retracted position to an advanced position to eject the plurality of staples from the staple cartridge;
a knife carrier supported within the through bore of the staple pusher and defining a central bore that receives the inner housing portion of the shell housing, the knife carrier movable about the inner housing portion between a retracted position and an advanced position, the knife carrier defining a pocket that receives the auxiliary detent when the knife carrier is in the retracted position to obstruct movement of the knife carrier from the retracted position towards the advanced position; and
a knife supported on the knife carrier.

13. The reload assembly of claim 12, wherein the knife carrier includes an inner surface that defines the central bore of the knife carrier, the inner surface of the knife carrier supporting at least one primary detent, the inner housing portion of the shell housing including an outer surface that defines at least one longitudinal recess that receives the at least one primary detent, the at least one primary detent having a proximal portion, a distal portion, and an abutment surface that separates the proximal portion of the at least one recess from the distal portion of the at least one recess, wherein the at least one primary detent moves into an interference fit with the abutment surface as the knife carrier is moved from its retracted position towards it advanced position.

14. The reload assembly of claim 12, wherein the auxiliary detent is resilient and includes a spring clip.

15. The reload assembly of claim 12, wherein the auxiliary detent is rigid.

16. The reload assembly of claim 12, wherein the knife carrier includes a plurality of resilient longitudinal body portions that define the central bore, each of the longitudinal body portions being spaced from adjacent longitudinal body portions to define longitudinal slots.

17. The reload assembly of claim 12, wherein the pocket is defined in adjacent longitudinal body portions of the knife carrier and communicates with a respective one of the longitudinal slots such that the auxiliary detent is aligned with the respective one of the longitudinal slots, the auxiliary detent being movable into the respective one of the longitudinal slots as the knife carrier moves from its retracted position towards its advanced position.

18. The reload assembly of claim 17, wherein the width of the auxiliary detent is greater than the width of the respective one of the longitudinal slots such that movement of the auxiliary detent through the respective one of the longitudinal slots causes outward deformation of the adjacent longitudinal body portions.

19. The reload assembly of claim 12, further including a bushing secured to the inner housing portion of the shell housing, wherein the auxiliary detent is supported on the bushing.

* * * * *